(12) United States Patent
Phan

(10) Patent No.: US 9,555,165 B2
(45) Date of Patent: Jan. 31, 2017

(54) MEDICAL TUBING FOR CATHETERS

(75) Inventor: Huy Phan, Santa Clara, CA (US)

(73) Assignee: Cordis Corporation, Fremont, CA (US)

( * ) Notice: Subject to any disclaimer, the term of this patent is extended or adjusted under 35 U.S.C. 154(b) by 907 days.

(21) Appl. No.: 13/239,916

(22) Filed: Sep. 22, 2011

(65) Prior Publication Data

US 2013/0006174 A1 Jan. 3, 2013

Related U.S. Application Data

(60) Provisional application No. 61/503,511, filed on Jun. 30, 2011.

(51) Int. Cl.
| | | |
|---|---|---|
| *A61M 25/00* | (2006.01) | |
| *A61L 29/14* | (2006.01) | |
| *A61L 29/06* | (2006.01) | |
| *A61L 29/04* | (2006.01) | |
| *A61M 25/10* | (2013.01) | |
| *A61M 25/01* | (2006.01) | |

(52) U.S. Cl.
CPC ............. *A61L 29/14* (2013.01); *A61L 29/049* (2013.01); *A61L 29/06* (2013.01); *A61M 25/0043* (2013.01); *A61M 25/1006* (2013.01); *A61M 2025/0039* (2013.01); *A61M 2025/0059* (2013.01); *A61M 2025/0183* (2013.01)

(58) Field of Classification Search
CPC ............. A61M 2025/0039; A61M 2025/0059; A61M 25/0043; A61M 25/1006; A61M 2025/0183; A61L 29/049
USPC ................................................ 604/96.01, 525
See application file for complete search history.

(56) References Cited

U.S. PATENT DOCUMENTS

| | | | |
|---|---|---|---|
| 4,883,468 A | 11/1989 | Kousai et al. | |
| 5,772,641 A | 6/1998 | Wilson | |
| 5,964,778 A | 10/1999 | Fugoso et al. | |
| 6,554,841 B1 * | 4/2003 | Yang | 606/108 |
| 6,814,744 B2 * | 11/2004 | Yang et al. | 606/194 |
| 2003/0065352 A1 | 4/2003 | Yang et al. | |
| 2003/0114794 A1 | 6/2003 | Duchamp | |
| 2005/0215942 A1 | 9/2005 | Abrahamson et al. | |

(Continued)

FOREIGN PATENT DOCUMENTS

| | | |
|---|---|---|
| EP | 0914836 A2 | 5/1999 |
| JP | H04221571 A | 8/1992 |

(Continued)

OTHER PUBLICATIONS

Written Opinion of the Int'l Searching Authority for International Appln. No. PCT/US2012/042924, dated Aug. 8, 2012.

*Primary Examiner* — Kevin C Sirmons
*Assistant Examiner* — Deanna K Hall
(74) *Attorney, Agent, or Firm* — Khoi Q Ta

(57) ABSTRACT

Tubing made of two or more polymers circumferentially arranged around the perimeter of the tubing in a single layer may be useful as medical tubing. Specifically, such tubing may be useful in catheters, sheaths, sheath introducers, implant delivery systems, and other medical devices having elongated tubular components. Selection of the two or more polymers based on the durometer and melting temperature permits optimization of axial strength and flexibility for particular applications. Such tubing may be extruded as a single layer tubing or a multi-layer tubing where the additional layers may be single material layers or more multi-polymer layers.

6 Claims, 4 Drawing Sheets

(56) References Cited

U.S. PATENT DOCUMENTS

2009/0105652 A1    4/2009  Beal et al.
2012/0316585 A1*  12/2012  Jeffrey ................ A61M 25/005
                                                                         606/159

FOREIGN PATENT DOCUMENTS

| JP | H0938209 A | 2/1997 |
| JP | H11192300 A | 7/1999 |
| JP | 2002143314 A | 5/2002 |
| JP | 2004508881 A | 3/2004 |
| JP | 2005503898 A | 2/2005 |
| JP | 2006501935 A | 1/2006 |
| JP | 2008539049 A | 11/2008 |

* cited by examiner

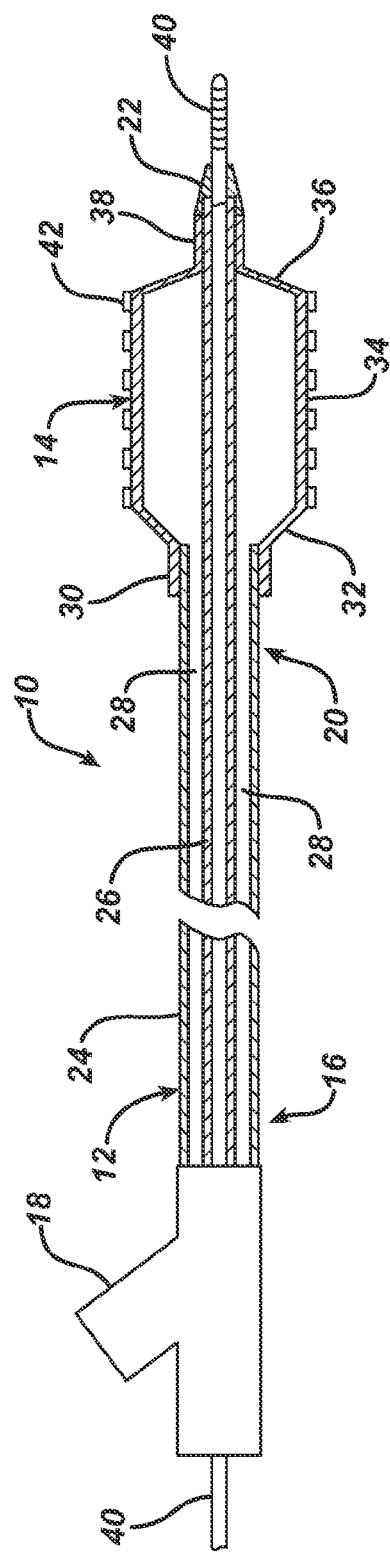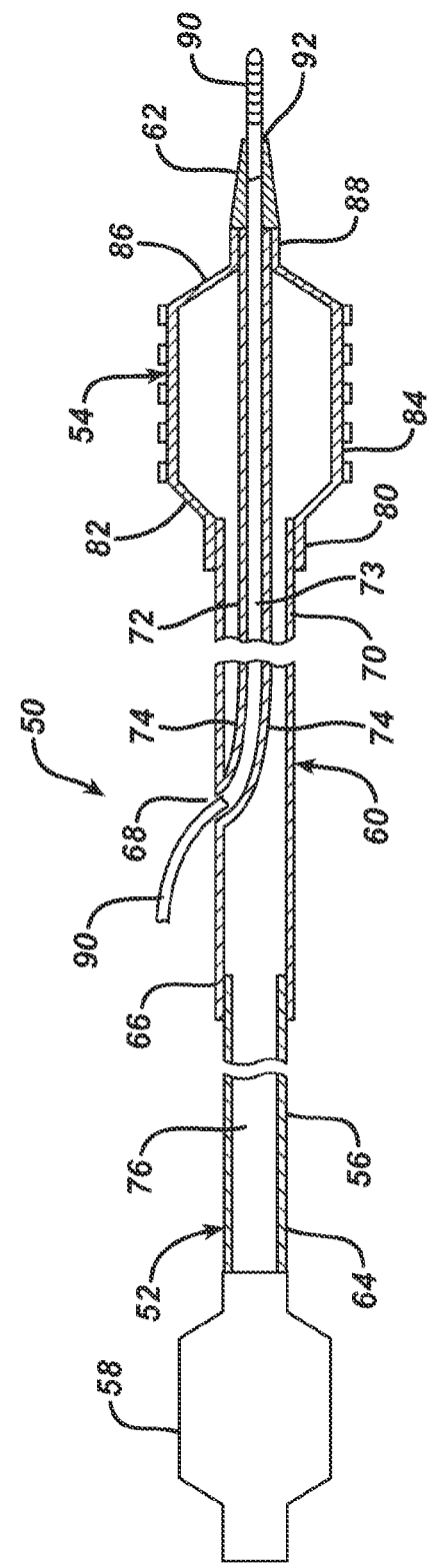

MEDICAL TUBING FOR CATHETERS

RELATED APPLICATIONS

This application claims the benefit of priority under 35 U.S.C. §119 of U.S. Provisional Application No. 61/503,511, which was filed on Jun. 30, 2011, the entirety of which is incorporated by reference.

BACKGROUND

1. Technical Field

The invention relates to the field of medical tubing, and more particularly medical tubing suited for catheters and other elongated medical devices.

2. Related Devices and Methods

Vascular disease is a leading cause of premature mortality in developed nations. Treatment of vascular disease may include implantation of tissue supporting stents or prosthetic vasculature, e.g., grafts, stent-grafts, etc., which are delivered through the vasculature at a reduced dimension for ease of navigation in, and reduced chance of injury to, the tortuous vasculature from entry point to the diseased location. Such treatment may include angioplasty performed by expanding a compliant, semi-compliant, or non-compliant balloon in narrowed vessels, which may be narrowed for one or more reasons including the presence of a calcified lesion. These treatments are delivered using a catheter designed to be advanced through the vasculature from a point of entry to the site where the treatment is needed. Such catheters typically include an elongated shaft with a distal end, which is the end furthest from the medical professional advancing the catheter. Such shafts may have variable designs as best suited to deliver the desired treatment from the point of entry to the vasculature to the intended implantation site. Some devices include additional features such as tapered tips on the distal ends of the elongated shafts, sheaths or outer members disposed about much of the length of the elongated shaft and about the vascular implant, and various features on the proximal end, that is, the end closest to the medical professional to perform varied functions, e.g., release of dye or other visualization agent, valved access to a lumen running through the elongated shaft for inserting a guide wire, sealed attachment of a pressurized fluid to inflate balloons at the distal end, or other mechanisms involved in the controlled delivery of the treatment to its intended site. This disclosure describes medical tubing useful as one or more components of such medical devices, including catheters. Unless otherwise stated, the other structural variations in the construction of the catheters of which the present invention is a component are not germane to the present invention.

In many cases, the catheter is an elongated device, which includes one or more elongated tubular members. It may have an elongated balloon at or near its distal end. It may have a tubular member having a lumen through which the catheter follows the path of a previously placed guide wire in the vasculature. Such a tubular member is often referred to as a guide wire tube. The catheter may additionally have another tubular member having a proximal end and a distal end and a lumen therethrough, and surrounding a length of the guide wire tube, but having a different inner diameter than the outer diameter of the guide wire tube such that a roughly annular lumen remains. Such a tubular member is sometimes referred to as an outer member, and the guide wire tube may then alternately be referred to as an inner member. The guide wire tube or inner member may extend distally of the distal end of the outer member. An inflatable member may sealingly surround at its proximal end the external surface of the distal end of the outer member and the external surface of the distal end of the inner member at its (the inflatable member's) distal end. Such sealing may be accomplished by thermal bonding of bondable materials or through the use of a tie layer or adhesive between concentric surfaces. Such a fluid-tight attachment of the inflatable member to the inner and outer member places the interior of the inflatable member in fluid communication with the substantially annular lumen formed between the inner member and the outer member. A typically much shorter length (than either the inner or outer member's length) and separate tubular member having a proximal end and a distal end and a lumen therethrough may have a tapered outer surface and may be attached to the distal end of the elongated shaft, either through a butt joint with the annular surface of the distal end of the inner member or through a lap joint with the outer cylindrical surface of the distal end of the inner member. Alternate attachment constructions of distal tips to the distal end of the catheter are known in the art. For example, see U.S. Pat. Pub. No. 2003/0114794 A1 and U.S. Pat. No. 5,964,778 to Fugoso et al., which are expressly incorporated by reference to the extent not contradictory to the remainder of the present specification.

Balloon catheters used to perform angioplasty in coronary arteries are sometimes referred to as percutaneous transluminal coronary angioplasty ("PTCA") catheters. These catheters are inserted at a point of entry in a peripheral artery, e.g., a radial or femoral artery, and advanced "upstream" through the arteries to the aorta and to the ostium of the specific coronary artery in need of treatment. The force to advance the catheter is applied external to the patient on an external portion of the catheter, and the force is transferred to the distal tip of the catheter as a result of the column strength or axial stiffness of the catheter. The stiffer the catheter, the easier to advance the distal tip and any therapeutic device or beneficial agent to the desired site. The quality of being able to push a proximal portion of the elongated shaft and have the distal tip move along an artery the same distance is commonly referred to as "pushability." However, a vascular balloon catheter also has the need to track closely to a guidewire that is resident in the arterial network and follows the tortuous path of the arteries. That quality is commonly called "trackability." Axial flexibility is needed to have high trackability, and therefore closely track a tortuously curved guidewire. Yet another desirable characteristic of a vascular balloon catheter designed to traverse a calcified lesion or other stenotic area in a coronary artery or other blood vessel is called "crossability," or, i.e., the catheter's ability to have the distal tip cross the stenosis by the medical professional pushing on the proximal end or some external (to the patient) portion of the catheter.

PTCA catheters that advance through the arteries by sliding over a previously placed guide wire have two commercially available variations, in terms of whether the entire (or almost the entire) length of the catheter slides over the guide wire, or whether only a shorter length of the catheter, at its distal end, slides over the guide wire. Another way to express the difference between the two constructions is whether the guide wire lumen runs the entire length of the catheter and has a proximal port in the proximal end (or in one of the two ports present in the commonly used Y connectors) of the catheter, or whether the proximal port of the guide wire lumen is closer to the distal end of the catheter than the proximal end, and generally between 9 and 20 centimeters proximal of the distal end, or even closer, such as at the proximal end of the inflatable member. The case where the guide wire runs through the entire catheter, or i.e., the guide wire lumen runs through the entire length of the catheter is commonly called an "over-the-wire" ("OTW") catheter. The case where the guide wire runs through a shorter length of the catheter near the distal end, or i.e., the guide wire lumen has a proximal port closer to the distal end than the proximal end is commonly called a "rapid-exchange" or "Rx" catheter. Another known term for the second case is single-operator-exchange ("SOE") catheter.

It is common in either type of PTCA catheter, OTW or Rx, to have a proximal portion with greater axial stiffness and a distal portion with a lower relative axial stiffness. This may be accomplished by a tapered support mandrel extending from the proximal end to a point proximal of the distal end, or selection of tubular segments with gradually decreasing column strength. In Rx catheters, it is common to use a relatively stiff proximal tubular member (shaft), such as a metal hypotube, and to attach a relatively less stiff (more flexible) polymer shaft to the distal segment of the hypotube. There may be additional metal or polymer members (e.g., stiffening wires, support tubes, reinforcing tubes, support mandrels, coils, patterned perforations in or "skived" sections of the hypotube, etc.) in Rx designs to provide a gradual transition in axial stiffness to the catheter as a whole from a relatively constant high stiffness proximal shaft to at least the proximal port of the guide wire lumen, which is present along side, or in the side of, the outer member. Without such a transition, the abrupt change in column strength between the end of the hypotube and the proximal port of the guidewire results in a tendency of the catheter to close the inflation lumen when the catheter buckles or kinks in that section of the catheter as a result of the axial loading, which closure of the inflation lumen is undesirable. The distal shaft of an Rx PTCA catheter, as with the distal portion of an OTW PTCA catheter, is generally more flexible, as this is the part that follows the aortic arch and is advanced through small coronary arteries, which tend to be rather tortuous in addition to having a much smaller diameter.

Two of the factors that influence the current PTCA catheter crossability are flexibility and pushability of the distal shaft of an Rx catheter or of the distal portion of an OTW catheter. For example, the more flexible a distal shaft or distal portion is, the higher the crossability of a catheter given the same axial stiffness, or i.e., pushability. Mechanically, however, a shaft that is flexible enough to track through tortuous vessels may not have the column strength to transmit sufficient force axially, while a stiff shaft can transmit greater force axially, but not be flexible enough track along the guidewire through a tortuous vessel. The trade off with increasing flexibility is the reduction of pushability and vice versa.

One commercially available design of the catheter inner body (yet another name for the inner member or guide wire tube), outer body (another name for the outer member), or tip includes a multilayer co-extrusion of different materials on top of each other, e.g., forming radial layers. There is a limitation to this multiple single-material-layer co-extrusion design in that the bending stiffness is uniform in 360 degrees.

The catheter tip is the first component of the catheter to encounter vessel tortuosity, vessel narrowing (stenosis), and calcified stenotic lesions. It is beneficial that the catheter tip is bendable to conform to smaller radius turns of the guide wire in the vasculature after the guide wire has been advanced from the point of entry to, and usually slightly past, the desired site of treatment. A stiff tip that does not conform to the guide wire can displace the guide wire position and may encounter difficulty in navigating through a vessel that has a sharp or abrupt turn. A tip made entirely of flexible material may also not perform as well as desired by "fishmouthing," a term used to describe when the normally circular cross section of the catheter becomes oval, which increases one dimension and decreases the dimension in the orthogonal direction. That decreased dimension may result in the catheter gripping the guide wire as the dimension approaches the outer diameter of the guide wire. A tip made entirely of flexible material may also fold back on itself, i.e., buckle or bunch up, or alteratively, it may flare, or even evert, which is also not desirable. Thus, it is desirable to have a tip construction that (1) can track gently over the guide wire without displacing the position of the guide wire, (2) minimize "fishmouthing", and (3) be able to push through stenotic lesions or between the stent struts without one or more of buckling, folding, flaring, or everting.

SUMMARY

A length of multi-durometer medical tubing in accordance with the invention comprises a first polymer having a first durometer and a first melting temperature and a second polymer having a second durometer different than the first durometer and a second melting temperature, where the first polymer and the second polymer are circumferentially arranged in discrete, axially oriented segments forming at least one layer of the tubing.

A medical device in accordance with the invention includes a length of medical tubing comprising a first polymer having a first durometer and a first melting temperature and a second polymer having a second durometer different than the first durometer and a second melting temperature, where the first polymer and the second polymer are circumferentially arranged in discrete, axially oriented segments forming at least one layer of the tubing.

A catheter in accordance with the invention comprises an elongated shaft having a distal end, an inflatable member attached to, and adjacent the distal end of, the elongated shaft, wherein the elongated shaft includes a tubular member made of at least a first polymer and a second polymer, the first and second polymer being in alternating, circumferentially arranged, discrete segments with the same radial thickness.

A catheter in accordance with the invention comprises an elongated shaft having a distal end, an inflatable member attached to, and adjacent the distal end of, the elongated shaft, wherein the inflatable member includes a tubular member made of at least a first polymer and a second polymer, the first and second polymer being in alternating, circumferentially arranged, discrete segments with the same radial thickness.

These and other features, benefits, and advantages of the present invention will be made apparent with reference to the following detailed description, appended claims, and accompanying figures, wherein like reference numerals refer to structures that are either the same structures, or perform the same functions as other structures, across the several views.

BRIEF DESCRIPTION OF THE FIGURES

The figures are merely exemplary and are not meant to limit the present invention.

FIG. 1 illustrates an "over-the-wire" type balloon catheter or stent delivery system.

FIG. 2 illustrates a "rapid-exchange" type balloon catheter or stent delivery system.

DETAILED DESCRIPTION

Figure 3:
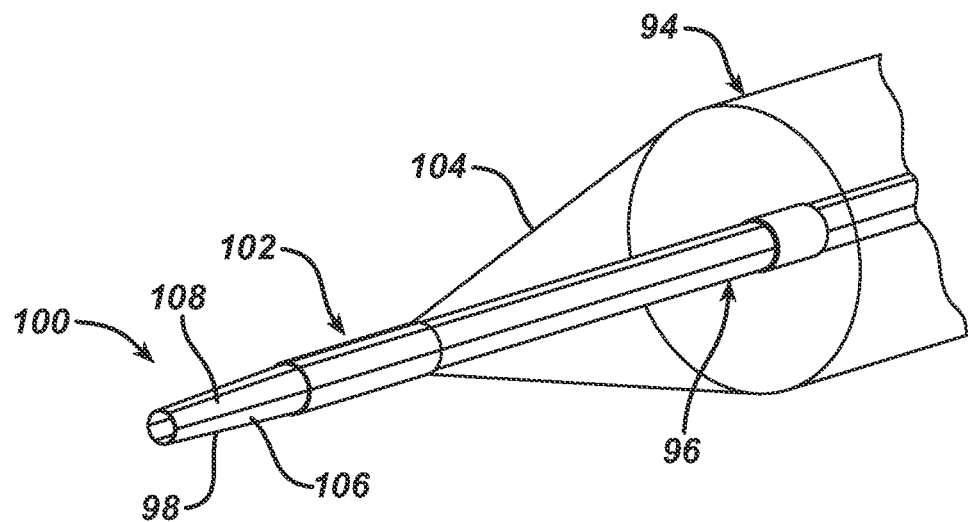
FIG. 3 illustrates a distal portion of a balloon catheter using an embodiment of the medical tubing as the inner body and unitary tapered distal tip.

The terms "tube" and "tubular" are used in their broadest sense, that is, any object which is arranged at a radial distance about a longitudinal axis. Accordingly, the terms "tube" or "tubular" include any structure that is (i) cylindrical or not, such as for example having an elliptical or polygonal transverse cross-section, or any other regular or irregular cross-section; (ii) has a changing or different cross-section along its length; (iii) is arranged around a straight, curved, bent, or discontinuous axis; (iv) has an imperforate, or a periodic or other perforate, irregular, or gapped surface or cross-section; (v) is spaced uniformly or irregularly, including being spaced varying radial distances from the longitudinal axis; or (vi) has any desired length or cross-sectional size.

One aspect of some embodiments of the invention is increased flexibility of the distal shaft and tip over current single or dual (concentric or radially arranged) single-material layer distal shafts and tips without sacrificing pushability. Current advancements in extrusion technology allow for single layer co-extrusion to produce a single lumen tubing with two or more polymers of different durometer side by side around the circumference or perimeter, and extending along the axial direction for the entire length, or parallel to the longitudinal axis of the tubing. Medical tubing according to the invention allows the softer/softest durometer polymer to control the bending property of the medical tubing and the harder/hardest durometer polymer to control the axial stiffness or strength for advancing across lesions or narrowed vessels. Such varied stiffness on the tubing shaft can overcome the limitation of the current single durometer tubing or radially arranged, multiple, single-durometer-material layer tubing.

Another aspect of some embodiments of the invention is increased flexibility of the tip material, yet minimized fish mouthing along the guide wire, and increased stiffness at the leading edge of the distal tip. Many softer durometer polymers tend to melt at a few degrees below many of the harder durometer polymers, and those softer polymers tend to flow more easily than those harder durometer polymers. When present, this difference in melt temperature ($T_m$) enables a thermal process of tapering the cylindrical tip that may displace (at least some of) the softer material and melt the harder durometer polymer together at the very distal (leading edge) portion of the distal tip, which is true whether the distal tip is a separate piece of tubing joined to the remainder of the components or just the distal end of the inner body (inner member or guide wire tube) or distal balloon leg, which is then processed further to form the tip. The latter described construction and process results in a unitary configuration of the tapered tip and some other component of the catheter, e.g., balloon or inner body). In other embodiments, the harder material blends with the softer material, displaced or not, at the distal (leading edge) during processing Methods of producing tapered tips are known to one of skill in the art, and include, but are not limited to (1) supporting the distal portion of the catheter on a mandrel, with optionally tapered tip, and placing a shrink tube over the assembly, and blowing hot air on the assembled shrink tube, distal tip tubing, and shaped mandrel until the shrink tube shrinks and the tubing melts to the shape of the mandrel; (2) use of a two or more part die around the tubing, which is supported either by one or more parts of the die or a mandrel, and then heating the die via conduction, RF, IR, or laser; and (3) use of a single piece mold, and heating in a fashion by one of the aforementioned methods with respect to a two or more part die. In all three methods described, the tubing has parts that are under pressure, and when heated, material in those parts will flow in a direction of least resistance, often backwards (proximally, to provide a radially thicker wall at a proximal portion, or radially inwards in cases, e.g., of tapered support mandrels. In these processes, it is envisioned that the material with the lower melt temperature will be the first to flow in the direction of least resistance and change the relative positioning and consitution of the polymer forming the distal tip.

Another aspect of some embodiments of the invention is enhanced lubricity of the inner diameter of the medical tubing created by extruding the soft section with an additive, resulting in a low coefficient of friction with the guidewire, vessel wall, or guide catheter without the need for a separate coating.

In some embodiments, the polymers of different durometers are co-extruded side by side around the circumference or perimeter of single lumen tubing. The alternating hard and soft axial co-extrusion allows for flexible tubing with a surprisingly high pushability characteristic. Such a co-extrusion may be used as a catheter component, for instance, an inner body, or an outer body, or both. The soft durometer portion of the catheter is selected for the desirable bending characteristics, and the hard durometer (relative to the soft durometer) polymer is selected for the desired axial pushability characteristics. With this design, the distal innerbody can then extend distally and become a desirable tip material.

Conventional catheter tips are typically made of a single material of a single durometer of a single lumen tubing. Another standard industry configuration is multiple single-material tubes of different durometer polymers aligned end-to-end along their longitudinal axes and then thermally bonded together to make a gradual increase in flexibility in the proximal-to-distal direction and in particular in the tip. The circumferentially arranged, multiple durometer configuration of medical tubing in accordance with the invention has a single extruded layer that introduces two or more materials to the tip without thermally bonding them together. The soft polymer extrudes along side the harder polymer, and provides the desired bending characteristic through curvy or tortuous turns, and the harder polymer provides the desired pushability characteristic for the catheter to transmit the external force through the tip and advance the catheter through the vasculature. The duality invites opportunities for different material properties for different sections of the tip, which can then be optimized for different purposes.

Besides providing the advantage of flexibility with pushable distal tip, medical tubing in accordance with the invention, when thermally processed to form the taper in the tip allows the softer material to be displaced from its location in between harder durometer material due to the softer material's typically lower melt temperature and lower viscosity flow. The harder material then melts together with the softer material that remains making the very distal portion of the tip gradually harder, approaching the durometer of the harder durometer polymer. This gradually harder tip allows for pushability through difficult calcified stenoses or total occlusion (whether chronic or acute) without fishmouthing, experiencing flare, folding back upon itself, or accordioning due to high axial forces against a tight lesion. In some embodiments, the reduced diameter tip may, at the distal tip after the tapering processing, be characterized by a blend of materials at any one location rather than distinct segments of one material only.

Exemplary materials for use in embodiments of the invention include polyamides ("PA") such as nylons, e.g. nylon 6/6, nylon 11, nylon 12, or polyether block amides ("PEBA") (such as PEBAX® PEBAs) in the durometer range from 25 D to 72 D (Shore hardness, D scale) inclusive, or urethanes in the durometer range from 75 A to 82 A (Shore hardness, A scale) inclusive.

When selecting the materials for use in embodiments of the invention, consideration can be given to the desired bond strength between the two materials. The closer in durometer the two materials are the greater the strength of the bond formed during extrusion. As the medical tubing when used as an outer body must withstand the pressurization of the inflation fluid for inflating the balloon, the bond strength must accommodate without failure the expected hoop stress for the maximum expected inflation pressure. Thus weak bonds are not desirable. When the medical tubing is used as a guide wire lumen, it must withstand the pressurization of the inflation fluid in compression, as well as the force of the catheter on the guide wire without separating. Again, weak bonds are not desirable. When the medical tubing is used to form the distal tip of a catheter, it must retain the guidewire within its lumen without splitting, and thus strong bonds must be maintained.

In view of the need for strong bonds between the different durometer materials, in some embodiments, the difference in durometer is at most 25 or at most 20.

Another factor for selecting materials for use in medical tubing according to the invention is the melting temperature of each material. Similar to the discussion of durometer, smaller differences in melt temperature improve the bond strength and overall ease of further processing for example, tapering the tubing to form a tapered distal tip.

In some embodiments, the difference in melt temperature is up to and including twenty degrees Celsius (20° C.). In some embodiments, the difference in melt temperature is up to and including five degrees Celsius (5° C.). In some embodiments, the difference in melt temperature is within a few degrees (e.g., 0+/−3.0° C.).

In some embodiments, the difference in melt temperature is up to and including twenty degrees Fahrenheit (20° F.). In some embodiments, the difference in melt temperature is up to and including five degrees Fahrenheit (5° F.). In some embodiments, the difference in melt temperature is within a few degrees (e.g., 0+/−3.0° F.).

In some embodiments, at least one of the two different durometer materials can have an additive to improve the lubricity of the tubing to reduce the coefficient of friction (static or kinetic) with respect to another object (guide wire, guide catheter, vessel wall, etc) Enhanced lubricity as the result of an additive need not be present in both durometer materials in order to effectively provide a lubricous surface (whether for sliding contact with the vessel, guide catheter or guide wire). In some embodiments, only the softer durometer material has an additive to improve the lubricity of the medical tubing. In some embodiments, only the harder durometer material has an additive to improve the lubricity of the medical tubing.

Examples of additives for possible inclusion include a hydrogel, a hydrophilic material, a hydrophobic material, such as PTFE or HDPE. The additive may be chemically bonded to the softer durometer material, or present therein as a blend or as discrete particles, to enhance lubricity.

In embodiments with only two materials of differing durometers, the soft-hard alternating pattern can be 2×2 (hard, soft, hard, soft) or 3×3 (hard, soft, hard, soft, hard, soft), etc.

In some embodiments, the soft durometer material segment can be one half the arc length of the hard durometer material segment for high pushability with moderate bending. In some embodiments, the soft durometer material segment's arc length may be up to 2 times the harder durometer material segment's arc length for highly flexible tubing with moderate pushability.

Medical tubing according to some embodiments of the invention is not limited to single layer extrusions. For example, a second concentric layer may be co-extruded on top, or bottom, or a third concentric layer may be co-extruded resulting in the axially arranged multi-polymer layer may be in any one of the three concentric layers. The additional layer(s) may be also dual-durometer material layers or single durometer material layers. The additional layer(s) may have a different wall thickness than the first layer, or it may have the same wall thickness as the first layer.

In dilatation catheters, wall thickness of medical tubing according to the invention may be anywhere in the range of 0.001" to 0.004".

In sheaths or guiding catheters, wall thickness of medical tubing according to the invention may be anywhere in the range of 0.002" to 0.010".

Inner and outer diameters are dependent on the vessels through which the catheter or medical device is intended, or the accompanying medical devices used with the medical tubing, e.g., the diameter of guide wires, which range from 0.010" to 0.038" in some embodiments, and include 0.014" and 0.018", among diameters, or the inner diameter of guiding catheters, etc.

In some embodiments, the circumferentially arranged multi-durometer medical tubing can be used a tip material bonded to a standard single durometer inner body at the distal balloon leg seal.

In some embodiments, the circumferentially arranged multi-durometer polymers can each have a different color added for distinction between product (e.g., producing blue and white striped tubing vs. red and black striped tubing that indicates a different size or different trackability/pushability/crossability characteristics between the two products).

In some embodiments, the distal tip section can be thermally tapered whereas the harder durometer material will fuse together to make a stiff tip for anti-fishmouthing and resistance to lift or peel back when encountering calcified stenotic lesions or stent struts.

The axially oriented, circumferentially arranged, multi-durometer design can be extruded into a parison and blown into a multi-durometer balloon. The extrusion can be designed to enhance balloon flexibility and permit non-circular and non-uniform expansion according to some variable, e.g., pressure or temperature.

DETAILED DESCRIPTION OF THE FIGURES

Turning now to the embodiments illustrated in the figures, FIG. 1 illustrates an "over the wire" type balloon catheter 10. Catheter 10 includes an elongated shaft 12 and an inflatable member 14 attached on a distal portion of elongated shaft 12. As illustrated, catheter 10 has a proximal portion 16, a Y-connector 18 at its proximal end, and a distal portion 20 with a distal tip 22 at its distal end. Elongated shaft 12 is comprised of an outer tubular member 24 surrounding an inner tubular member 26. Outer tubular member 24 has a proximal end, a distal end, and a lumen therethrough. Inner tubular member 26 has a proximal end, a distal end, and a lumen therethrough. A length of inner tubular member 26 is co-extensive with outer tubular member 24 and where co-extensive they define an inflation lumen 28 with a substantially annular cross section. Inflation lumen 28 is in fluid communication with one of the two lumens of Y-connector 18 and with the interior of the inflatable member 14. Inner tubular member 26 extends distal of the distal end of outer tubular member 24. Inflatable member 14 has a proximal leg 30, a proximal cone 32, a working length 34, a distal cone 36, and a distal leg 38. Proximal leg 30 is coupled to a distal portion of outer tubular member 24 either indirectly with adhesive or a tie layer, or directly fusion or thermally bonded thereto. Distal leg 38 is coupled to a distal portion of inner tubular member 26 either indirectly with an adhesive or an additional tubular component, or directly fusion or thermally bonded thereto. As illustrated, distal tip 22 is a separate piece bonded via adhesive or thermal fusion to adjacent catheter components. A guide wire 40 is through the entire length of catheter 10 with only a proximal portion extending proximal of the proximal end of the other connector of Y connector 18 and a distal tip illustrated for clarity of other components.

As depicted in FIG. 1, catheter 10 is a stent delivery system, and illustrates a stent 42 about the inflatable member at its fully expanded diameter.

Any one of or all of outer tubular member 24, inner tubular member 26, and distal tip 22 of catheter 10 may be formed of embodiments of the medical tubing described herein.

FIG. 2 depicts a "rapid-exchange" type catheter 50. Catheter 50 includes an elongated shaft 52 and an inflatable member 54 attached on a distal portion of elongated shaft 52. As illustrated, catheter 50 has a proximal shaft 56, a hub 58 at its proximal end, and a distal shaft 60 with a distal tip 62 at its distal end. Proximal shaft 56 includes a hypotube 64, to which a polymer transition tube 66 is attached near the distal end of hypotube 64. One or more transition members (not illustrated) may be present in transition tube 66, inside the lumen of transition tube 66, or outside of transition tube 66, and may gradually change the axial stiffness between a high value of hypotube 64 to a value closer to lower value of the distal shaft 60 along the axial length of elongated shaft 52 from the end of the proximal shaft to at least the start of proximal guide wire port 68. Transition tube 66, optional transition member (not illustrated), inner body 72 and outer body 70 are joined to form proximal guide wire port 68. A distal outer body 70 surrounds a length of an inner body 72. Distal outer body 70 has a proximal end, a distal end, and a lumen therethrough. Inner body 72 has a proximal end, a distal end, and a lumen 73 therethrough, which serves as a guide wire lumen. A length of inner body 72 is co-extensive with distal outer body 70 and where co-extensive and distal of the guide wire port, they define an inflation lumen 74 with a substantially annular cross section Inflation lumen 74 is in fluid communication with lumen 76 of the hypotube 64, which is also an inflation lumen, and with the interior of the inflatable member 54. Inner body 72 extends distal of the distal end of distal outer body 70. Inflatable member 54 has a proximal leg 80, a proximal cone 82, a working length 84, a distal cone 86, and a distal leg 88. Proximal leg 80 is coupled to a distal portion of distal outer body 70 either indirectly with adhesive or a tie layer, or directly fusion or thermally bonded thereto. Distal leg 88 is coupled to a distal portion of inner body 72 either indirectly with an adhesive or an additional tubular component, or directly fusion or thermally bonded thereto. As illustrated, distal tip 62 is a separate piece bonded via adhesive or thermal fusion to adjacent catheter components. A guide wire 90 is through a distal length of catheter 50 with only a proximal portion extending proximal of the proximal guide wire port 68 and a distal tip extending distal of distal guide wire port 92 illustrated for clarity of the other components.

As depicted in FIG. 2, catheter 50 is an implant delivery system, and illustrates a implant 93 about the inflatable member at its fully expanded diameter.

Any one or all of distal outer body 70, inner body 72, and distal tip 62 of catheter 50 may be formed of embodiments of the medical tubing described herein.

FIG. 3 depicts a distal portion of an inflatable member 94, inner body 96, and tapered distal tip 98 of a catheter 100 according to the invention Inflatable member has a distal leg 102, a distal cone 104, a working section (only the distal portion of which is shown), a proximal cone (not shown), a proximal leg (not shown), and an inflated interior in fluid communication with a lumen in a proximal portion of catheter 100 (whether an OTW or Rx design). Distal leg 102 sealingly surrounds inner body 96, and tapered distal tip 98 extends distal of the seal between distal leg 102 and inner body 96, but distal tip 98 is unitary with inner body 96, having been shaped by a distal tip shaping process as known to one of skill in the art. The dark sections of inner body 96 in FIG. 3 are made of the harder durometer material 106, and the light sections of inner body 96 in FIG. 3 are made of a softer durometer material 108, which have been co-extruded around the circumference to form a single layer, multi-durometer tube.

Figure 4:
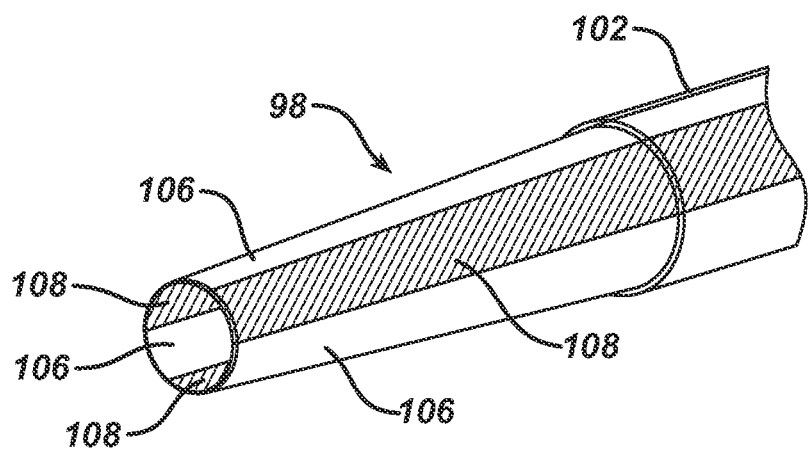
FIG. 4 illustrates an enlarged portion of FIG. 3.

FIG. 4 depicts an enlargement of tip 98 and part of the distal leg 102 of the inflatable member 94 of FIG. 3 and shows the reduced diameter of the distal end or leading edge of distal tip 98. As depicted, three sections of softer durometer material 106 alternate with three sections of harder durometer material 108. With reference to a section of material 106, the arc at the distal end or leading edge of distal tip 98 is shorter (narrower) and has a smaller radius or at least a smaller outer radius than at the proximal end of distal tip 98. As discussed above, due to thermal forming processes, the boundaries of the different durometer materials may not be as clear in actual parts.

Figure 5:
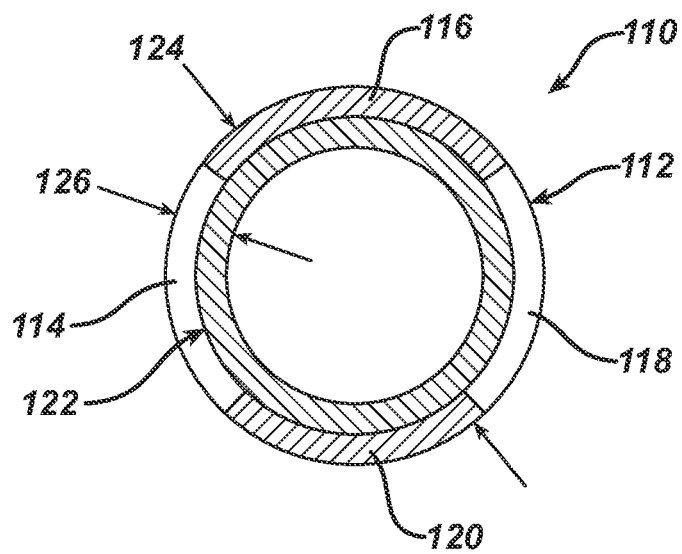
FIG. 5 illustrates a cross-section of another embodiment of the medical tubing.

FIG. 5 depicts a cross section of an embodiment of the medical tubing for use as an outer body, inner body, distal tip, or other tubular component of a medical device. Tubing 110 is formed from two layers which may be co-extruded or assembled in other ways known to one of skill in the art. The outer of the two layers depicted, layer 112, is comprised of two different durometer polymers arranged in side-by-side fashion around the perimeter starting with a section 114 of softer durometer material at "9 o'clock", and going clockwise, followed by a section 116 of harder durometer material, followed by a section 118 of softer durometer material, followed by a section 120 of harder durometer material. In this embodiment, all sections have the same "width" and sections 116 and 120 are positioned across from one another, and sections 114 and 118 are positioned across from one another. The inner of the two layers depicted, layer 122, is comprised of a single durometer material, and the durometer may be different from either the durometers of the softer or harder durometer materials of layer 112. In some embodiments, the durometer of layer 122 is lower than the durometer of softer material in layer 112. In some embodiments, the durometer of layer 122 is the same as the durometer of softer material in layer 112. The tubing has an outer diameter 124, and a radial wall thickness 126.

Figure 6:
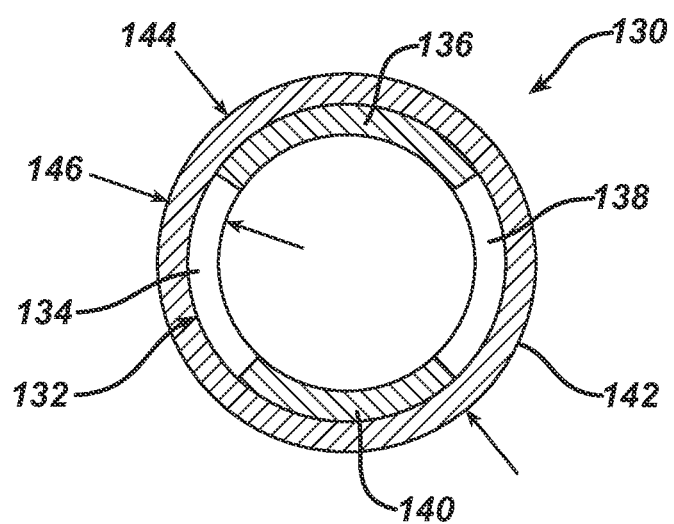
FIG. 6 illustrates a cross-section of yet another embodiment of the medical tubing.

FIG. 6 depicts a cross section of another embodiment of the medical tubing for use as an outer body, inner body, distal tip, or other tubular component of a medical device. Tubing 130 is formed from two layers which may be co-extruded or assembled in other ways known to one of skill in the art. The inner of the two layers depicted, layer 132, is comprised of two different durometer polymers arranged in side-by-side fashion around the perimeter starting with a section 134 of softer durometer material at "9 o'clock", and going clockwise, followed by a section 136 of harder durometer material, followed by a section 138 of softer durometer material, followed by a section 140 of harder durometer material. In this embodiment, all sections have the same "width" and sections 136 and 140 are positioned across from one another, and sections 134 and 138 are positioned across from one another. The outer of the two layers depicted, layer 142, is comprised of a single durometer material, and the durometer may be different from either the durometers of the softer or harder durometer materials of layer 132. In some embodiments, the durometer of layer 142 is lower than the durometer of softer material in layer 132. In some embodiments, the durometer of layer 142 is the same as the durometer of softer material in layer 132. The tubing 130 has an outer diameter 144 and a wall thickness 146.

Figure 7:
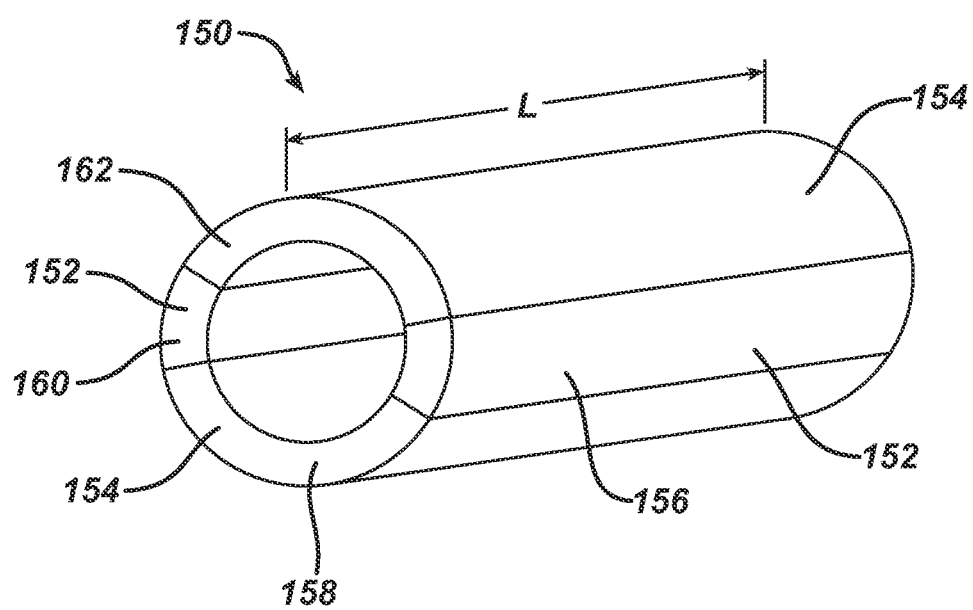
FIG. 7 illustrates a section of an embodiment of the medical tubing that may be joined to other catheter components to form a distal tip of the catheter.

FIG. 7 depicts a relatively short length of an embodiment 150 of the medical tubing for use as a distal tip, whether further processed to produce a taper or not, or other tubular component of a medical device. In this embodiment, the volumetric ratio of hard to soft durometer material is 3:1. The "arc width" of the hard segments is three times the "arc width" of the soft segments. Some embodiments of medical tubing have a length "L" that is in the range from 0.1 mm to 10 mm, inclusive. Discrete segments harder durometer material 152 alternates around the circumference in discrete segments of softer durometer material 154, and recognizing that the two materials are bonded together during extrusion, there may be an area between each set of the two discrete segments having some localized blending that does not take away from the description of discrete segments. Starting at "3 o'clock" and going clockwise, a narrow segment 156 of softer durometer material, followed by a wider segment 158 of harder durometer material, followed by a narrow segment 160 of softer durometer material, followed by a wider segment 162 of harder durometer material. Alternate configurations of alternating hard and soft segments arranged around the circumference of medical tubing 150 may be extruded.

Medical tubing according to embodiments of the invention may also be used in sheaths, sheath introducers, guide catheters, and implant delivery systems, such as, but not limited to, coronary or peripheral stents or abdominal aortic aneurism or thoracic aortic aneurism stent graphs. Medical devices, including, sheaths, sheath introducers, catheters, guide catheters, and implant delivery systems, for use in treating diseases and conditions of the neurovasculature, such as ischemic or hemorrhagic stroke, among others, would benefit from some embodiments of this invention, as the neurovasculature is rather tortuous.

Aspects of the present invention have been described herein with reference to certain exemplary or preferred embodiments. These embodiments are offered as merely illustrative, not limiting, of the scope of the present invention. Certain alterations or modifications which are possible include the substitution of selected features from one embodiment to another, the combination of selected features from more than one embodiment, and the elimination of certain features of described embodiments. Other alterations or modifications may be apparent to those skilled in the art in light of instant disclosure without departing from the spirit or scope of the present invention, which is defined solely with reference to the following appended claims.

The invention claimed is:

1. A catheter comprising:
an elongated shaft having a distal end, the elongated shaft including an outer tubular member having a proximal end, a distal end, and a lumen therethrough, an inner tubular member having a proximal end, a distal end, and a lumen therethrough for receiving a guide wire, wherein the outer tubular member surrounds at least a length of the inner tubular member and the inner tubular member extends distal of the distal end of the outer tubular member; and
an inflatable member adjacent the distal end of the elongated shaft, the inflatable member having a proximal end and a distal end, wherein the proximal end is attached to the outer member and the distal end is attached to the inner member;
wherein at least one of the outer tubular member and the inner tubular member includes a tubular member made of at least a first polymer with a first durometer and a second polymer with a second durometer different from the first durometer, the first and second polymer being in alternating, circumferentially arranged, discrete arc widths with the same radial thickness such that the arc width of a first polymer is three times the arc width of the second polymer.

2. The catheter of claim 1, wherein the tubular member is the outer tubular member.

3. The catheter of claim 1, wherein the tubular member is the inner tubular member.

4. A catheter comprising:
an elongated shaft having a distal end with a tapered distal tip;
an inflatable member attached to, and adjacent the distal end of, the elongated shaft;
wherein the tapered distal tip comprises a tubular member made of at least a first polymer with a first durometer and a second polymer with a second durometer different from the first durometer, the first and second polymer being in alternating, circumferentially arranged, discrete arc widths with the same radial thickness such that the arc width of a first polymer is three times the arc width of the second polymer.

5. The catheter of claim 4, wherein the elongated shaft includes an inner member and the tapered distal tip is unitary with the inner member, and the inner tubular member is the tubular member.

6. A catheter comprising:
an elongated shaft having a distal end;
an inflatable member attached to, and adjacent the distal end of, the elongated shaft;

wherein the inflatable member includes a tubular member made of at least a first polymer with a first durometer and a second polymer with a second durometer different from the first durometer, the first and second polymer being in alternating, circumferentially arranged, discrete arc width with the same radial thickness such that the arc width of a first polymer is three times the arc width of the second polymer.

\* \* \* \* \*